(12) United States Patent
Orikasa et al.

(10) Patent No.: US 6,644,968 B2
(45) Date of Patent: Nov. 11, 2003

(54) ORTHODONTIC APPLIANCE (75) Inventors: Masaaki Orikasa, Futaba-gun (JP); Seiji Kihara, Bizen (JP); Makoto Mitsudo, Akaiwa-gun (JP); Mitsuhiro Matsushima, Chiyoda-ku (JP)

(73) Assignee: Tomy Incorporated, Fukushima (JP)

( * ) Notice: Subject to any disclaimer, the term of this patent is extended or adjusted under 35 U.S.C. 154(b) by 0 days.

(21) Appl. No.: 10/062,427

(22) Filed: Feb. 5, 2002

(65) Prior Publication Data
US 2002/0168601 A1 Nov. 14, 2002

(30) Foreign Application Priority Data
Feb. 6, 2001 (JP) .................................... P.2001-029520

(51) Int. Cl.[7] .................................................. A61C 3/00
(52) U.S. Cl. ............................................. 433/8; 433/9
(58) Field of Search ........................................ 433/2–24

(56) References Cited

U.S. PATENT DOCUMENTS

| 5,573,401 A | * | 11/1996 | Davidson et al. | 433/8 |
| 5,595,484 A | * | 1/1997 | Orikasa et al. | 433/8 |
| 5,795,151 A | * | 8/1998 | Nonami et al. | 433/8 |

* cited by examiner

*Primary Examiner*—Cary E. O'Connor
(74) *Attorney, Agent, or Firm*—Sughrue Mion, PLLC (57) ABSTRACT

An orthodontic appliance comprising a main body for orthodontic treatment and a bonding base connected to the main body and capable of adhering to the teeth, wherein the main body and the bonding base each comprise calcium phosphate crystallizing glass. The calcium phosphate crystallizing glass preferably comprises CaO 10 to 60 wt %, $P_2O_5$ 25 to 85 wt %, $Al_2O_3$ 5 to 25 wt % and $Li_2O$ 0.01 to 5 wt %, and has Vickers hardness Hv based on JIS Z2244 of 4.5 GPa or lower, and bending strength based on JIS R1601 of 100 MPa or higher.

8 Claims, 7 Drawing Sheets

ORTHODONTIC APPLIANCE

FIELD OF THE INVENTION

The present invention relates to an orthodontic appliance adhered to teeth, such as a bracket, buccal tube, sheath, button or lingual attachment.

DESCRIPTION OF THE RELATED ART

Orthodontic appliances for use in orthodontic treatment been widely known, which comprise a main body capable of maintaining an archwire and a bonding base connected to the main body and capable of adhering to teeth. Those orthodontic appliances include bracket, buccal tube, sheath, button, lingual attachment and the like, and are appropriately selected according to orthodontic treatment methods.

In particular, the bracket is most ordinarily used in the following manner. The bracket is directly adhered to the patient's teeth with bonding base being inside. Archwire is mounted on the bracket thus adhered. As a result, external force is applied to malaligned teeth by the archwire, thereby correcting such malaligned teeth.

Metal brackets have conventionally been known as the ordinary bracket. Orthodontic appliances formed from transparent or white semi-transparent materials such as ceramic bracket or plastic brackets have recently been used for the purpose of improving aesthetic properties.

However, the ceramic bracket made of aluminum oxide or zirconium oxide is extremely hard in comparison with metal bracket, and is also harder than enamel of the teeth, so that there is the possibility of abrading enamel of the opposite teeth contacting the bracket when occluding. Especially, a deep bite has been a tabooing case evading the use of the ceramic bracket. To overcome such problems, U.S. Pat. No. 4,950,158 proposes a method of interposing an elastmeric cushion at a tiewing of incisal side.

In case of adhering a bracket having a slot in a main body and inlaying the archwire in the slot to perform the correction of dentition, the archwire should be slippery to the slot, because the teeth row is corrected by a restoring force of the archwire. However, the archwire is difficult to slide to the slot provided in the ceramic bracket, and friction between the bracket and the archwire is large, so that a problem occurred that it is difficult to exactly perform a desired correction of dentition. The main reason for this is assumed that since the ceramic bracket is very hard, the archwire creates biting at an end portion in the mesiodistal direction of the slot.

In view of the above problems, U.S. Pat. Nos. 5,358,402 and 5,380,196 disclose technologies, that a metal slot liner is attached to the ceramic bracket by means of, for example, brazing in order to improve the sliding property of the archwire within the slot. However, the ceramic bracket comprising inorganic materials such as aluminum oxide or zirconium oxide are difficult to bond to organic adhesives generally used for the orthodontic purposes. Therefore, it was necessary to apply a silane coupling agent to the bonding base, or weld glass frit or glass beads on the bonding base to form a mechanical lock thereon, thereby increasing bonding force to the organic adhesives. Treating the bonding base was a factor to increase production cost of the ceramic bracket.

When the bracket adhered on the teeth is debonded after orthodontic treatment, if the bracket is made of a metal, such a bracket can be debonded as if turning over the bonding base without injure the teeth. On the other hand, the ceramic bracket is harder than the metal bracket and the bonding base has an integral structure of the main body and has high rigidity. Therefore, extremely large force is required to debond the bracket, and there is the possibility of injuring enamel of the teeth. To overcome those problems, U.S. Pat. No. 5,439,379 proposes a method of crushing ceramic bracket at a central groove and debonding the same. Further, technologies of shielding a surface of a bonding base having dimples (U.S. Pat. No. 4,936,773) and a central part of a bonding base with an inert paint (U.S. Pat. No. 5,269,680) are to positively control a bonding/debonding strength.

On the other hand, the plastic bracket has a problem that the bracket is liable to deteriorate by absorbing water in the mouth during the orthodontic treatment and it is also liable to disintegrate before the completion of orthodontic treatment. In addition, the plastic bracket is liable to adsorb coloring agent contained in foods and drinks by water absorption, resulting in a further problem in deterioration of the aesthetic appreciation due to such a discoloration.

Polycarbonate brackets are widely known as such a plastic bracket. However, since such a bracket does not have sufficient strength to torque by rectangular archwires or ligation of a ligature wire, the bracket is generally reinforced with a metal insertion. For example, U.S. Pat. Nos. 4,299, 569 and 5,254,002 disclose plastic brackets having a metal slot liner as the insert arranged in mesiodistal direction of the bracket. Further, U.S. Pat. Nos. 5,595,484, 5,597,302 and 5,692,898 disclose plastic brackets formed by inserting metal members having U-shaped section in a direction crossing the slot.

Polycarbonate brackets having glass fibers mixed therewith for strength improvement are also known. The glass fibers contributes to improve strength of the bracket, but there is the problem that solvent cracks tend to occur due to influences by organic solvent components of an adhesive used for orthodontic application. It has been clinically known that the glass fiber reinforces the polycarbonate bracket, but on the other hand increases internal stress in the polycarbonate when molding, and microcracks occur due to the presence of a solvent in the adhesive or water-invasion with the passage of time, and as a result, the polycarbonate bracket deteriorates as being disintegrated.

A glass bracket is known as means for overcoming the problems involved in the ceramic and plastic brackets, and U.S. Pat. No. 5,261,814 discloses a bracket in which surface layer is crystallized under compression stress to form a reinforcing layer and the inside thereof is constituted of amorphous glass comprising the following compositions: $SiO_2$ 55 to 70%, $Al_2O_3$ 15 to 28%, ZnO 0 to 14%, $Li_2O_3$ 0 to 7%, $Na_2O$ 0 to 7%, $K_2O$ 0 to 3%, BaO 0 to 7%, MgO 0 to 7% and $TiO_2$ 0 to 7%.

However, this bracket is expensive because it is prepared from a glass sheet by a supersonic abrading process, a diamond cutting process or the like. Further, it is technically difficult to control thickness of the surface crystallized layer, and unevenness in thickness results in decreasing transparency (devitrification) and strength.

U.S. Pat. No. 5,795,151 describes a bracket comprising a diopside crystallizing glass (glass composition: $SiO_2$, MgO, $Al_2O_3$ and $TiO_2$). However, this bracket contains $Al_2O_3$ and $TiO_2$ in high contents. As a result, hardness of such a crystallizing glass is higher than that of the enamel of a natural tooth and there is the possibility of abrading enamel of the opposite teeth.

U.S. Pat. No. 4,784,606 describes a bracket comprising a glass tempered by ion exchange, where Li—Al—Si glass is dipped in a molten salt bath for 2 to 24 hours at temperatures higher than a strain point of the glass but lower than a softening point thereof, thereby obtaining the glass tempered by Naion. However, there is a problem that the ion-tempered layer is thin, and the bracket is worn in an early stage and is broken by occlusion or ligating.

U.S. Pat. No. 4,784,649 describes a bracket comprising a glass of a double crystal structure for the purpose of increasing strength. This glass has a large crystal structure in the inside of the glass, and has a small and flat crystal layer on the surface thereof, but a production process thereof is complicated. Further, not only cost is high but also strength is insufficient.

Thus, the glass bracket has disadvantages that its production process is complicated, its production technique is difficult, its production cost increases, and its strength and durability are insufficient as the orthodontic appliance.

The above-described problems occur all over the orthodontic appliances of the type which directly adhere to tooth crowns such as buccal tube, sheath, button or lingual attachment, in addition to the brackets.

SUMMARY OF THE INVENTION

The invention has been made in view of the above-described problems in the related art.

Accordingly, an object of the invention is to provide an orthodontic appliance having all of the following advantages 1) to 9):

1) production cost can be decreased;
2) aesthetic appreciation is excellent;
3) sufficient strength and durability are provided as the orthodontic appliance;
4) an allergy causing substance is difficult to generate;
5) the adhesion to the teeth is secured;
6) the opposite teeth are less to be worn during orthodontic treatment;
7) plague causing decayed teeth or periodontal diseases are difficult to adhere to the bracket during the orthodontic treatment;
8) debonding from the teeth is easy after the orthodontic treatment; and
9) in case that the orthodontic appliance allows engagement with the archwire for straightening the teeth, the sliding property is excellent to the archwire.

The invention provides an orthodontic appliance comprising a main body for orthodontic treatment and a bonding base connected to the main body and capable of adhering to teeth, wherein the main body and the bonding base each comprise a calcium phosphate crystallizing glass. Thus, because the main body and the bonding base each comprise the calcium phosphate crystallizing glass showing white and semi-transparency, the aesthetic appreciation of the orthodontic appliance is excellent.

Further, the bonding base comprising the calcium phosphate crystallizing glass does not require any special treatment as seen in ceramic brackets and can be securely adhered to the teeth with an adhesive for the orthodontic purpose, and the production cost of the orthodontic appliance can be decreased.

The calcium phosphate crystallizing glass orthodontic appliance does not require a metal insertion as seen in the plastic orthodontic appliances and also does not require any special treatment of forming a reinforced layer as seen in the conventional glass orthodontic appliance, but it has enough strength and durability as the orthodontic appliance. Therefore, the production cost of the orthodontic appliance can be decreased.

Further, since hardness of the calcium phosphate crystallizing glass can be determined so as to be equivalent to the hardness of enamel of the teeth, the opposite teeth can be prevented from wearing during the period of orthodontic treatment, and the orthodontic appliance can be easily debonded from the teeth without requiring excessive force after the orthodontic treatment.

The orthodontic appliance, in particular the tiewing, is sometimes disintegrated by unsuitable debonding operation, giving undue torque by the archwire, or unreasonable use of the wire cutter when cutting the ligature wire after ligating the archwire and the orthodontic appliance.

Even in such cases, the calcium phosphate crystallizing glass orthodontic appliances are comparatively grain-like in broken sections different from sharply broken sections as seen in soda lime glass widely known as general glass, and does not injure the mucous membrane in the mouth.

In addition, plague causing decayed teeth or periodical diseases is difficult to adhere to the calcium phosphate crystallizing glass orthodontic appliance.

According to the calcium phosphate crystallizing glass orthodontic appliance, it is not necessary to positively insert the metal liner as described above, and it is possible to provide the orthodontic appliance difficult to generate the allergy causing substance as represented by, for example, nickel.

The preferred embodiments of the invention are described below.

The calcium phosphate crystallizing glass comprises CaO 10 to 60 wt %, $P_2O_5$ 25 to 85 wt %, $Al_2O_3$ 5 to 25 wt % and $Li_2O$ 0.01 to 5 wt %. By preparing the calcium phosphate crystallizing glass having the above composition, the orthodontic appliance has high crystallizing rate particularly in crystallization, generates a fine and close crystallized structure, obtains high strength and a proper hardness not causing dental attrition to the enamel of the teeth, and has the transparency approximate to the enamel in spite of high crystallinity.

The orthodontic appliance is constituted such that Vickers hardness Hv based on JIS Z2244 of the calcium phosphate crystallizing glass is 4.5 GPa or lower, and bending strength based on JIS R1601 of the calcium phosphate crystallizing glass is 100 MPa or higher. According to this constitution, Vickers hardness of the calcium phosphate crystallizing glass is 4.5 GPa or lower, and is not too hard in comparison with Vickers hardness Hv (around 3.4 to 3.8 GPa) of the enamel of the teeth. Thus, during the orthodontic treatment, the possibility of injuring enamel of the opposite teeth can be securely decreased, and after the orthodontic treatment, the orthodontic appliance can be easily debonded from the teeth without requiring excessive force.

The bending strength of the calcium phosphate crystallizing glass is 100 MPa or higher, so that the orthodontic appliance has the sufficient strength to the torque by the archwire or the ligation of the ligature wire, and the possibility of disintegrating the orthodontic appliance during the orthodontic treatment can be surely decreased.

The main body and the bonding base are integrally formed with the calcium phosphate crystallizing glass having the same components, and the orthodontic appliance is constituted such that adhesive strength between the teeth and the bonding base is 7 MPa or higher per unit area. By making the adhesive strength 7 MPa or higher, even if a patient takes an ordinary meal, the adhesion can be securely maintained for a period of 18 to 24 months, which is considered as a general period of orthodontic treatment.

Surface roughness based on JIS B0601 of the bonding base is 10 μm or more. According to this feature, a substantial adhesion area between the bonding base and the adhesive for the orthodontic treatment is increased, and at the same time an anchoring effect can be obtained, so that the orthodontic appliance can be more securely adhered to the teeth. The surface roughness of the above-described range can be suitably accomplished by an ordinary phosphorous acid etching. This phosphorous acid etching can easily be operated by a doctor at a chair side, and the bonding base surface of an orthodontic appliance is made rough by sandblasting and then subjected to the phosphorous acid etching as a pre-treatment of adhesion. This is very useful to increase the adhesive force.

The main body has slots as orthodontic means. According to this constitution, the slot comprises the calcium phosphate crystallizing glass, and when the archwire is inlaid in the slot for performing the orthodontic treatment, the sliding property of the archwire to the slot is equal to or more than that of the metal slot and is excellent. In particular, it is possible to provide the orthodontic appliance difficult to generate the allergy causing substance as represented by, for example, nickel.

The orthodontic appliance is constituted such that dynamic frictional force when an archwire is pressed against the bottom of the slot at 1.96 N (200 gr), is 0.98 N (100 gr) or lower. According to this feature, the sliding property of the archwire to the slot can be securely made excellent.

The slots are provided in the inside thereof with a metal slot liner of U shaped cross section.

The reinforcement generally regarded as being essential, of the plastic bracket by the metal insertion tends to decrease the aesthetic appreciation and increase the production cost. Further, if the insert is made of a stainless steel, metal-allergy is caused by nickel or chromium.

However, the calcium phosphate crystallizing glass has enough strength in comparison with plastics, and the reinforcement by the metal insertion is not always necessary, but depending on kinds and shapes of the teeth to which the bracket is adhered, and types of orthodontic treatment, when it is desired to increase strength of the bracket, the arrangement of the metal slot liner is effective.

According to the above constitution, the sliding property of the archwire to the slot is excellent, and the orthodontic appliance of high strength can be provided.

Description of the Reference Numerals

1: main body
2: bonding base
3: archwire
10, 30: bracket (orthodontic appliance)
11: teeth
21: slot
32: metal slot liner

DETAILED DESCRIPTION OF THE INVENTION

The preferred embodiments of the invention will be explained by reference to the accompanying drawings.

Figure 1:
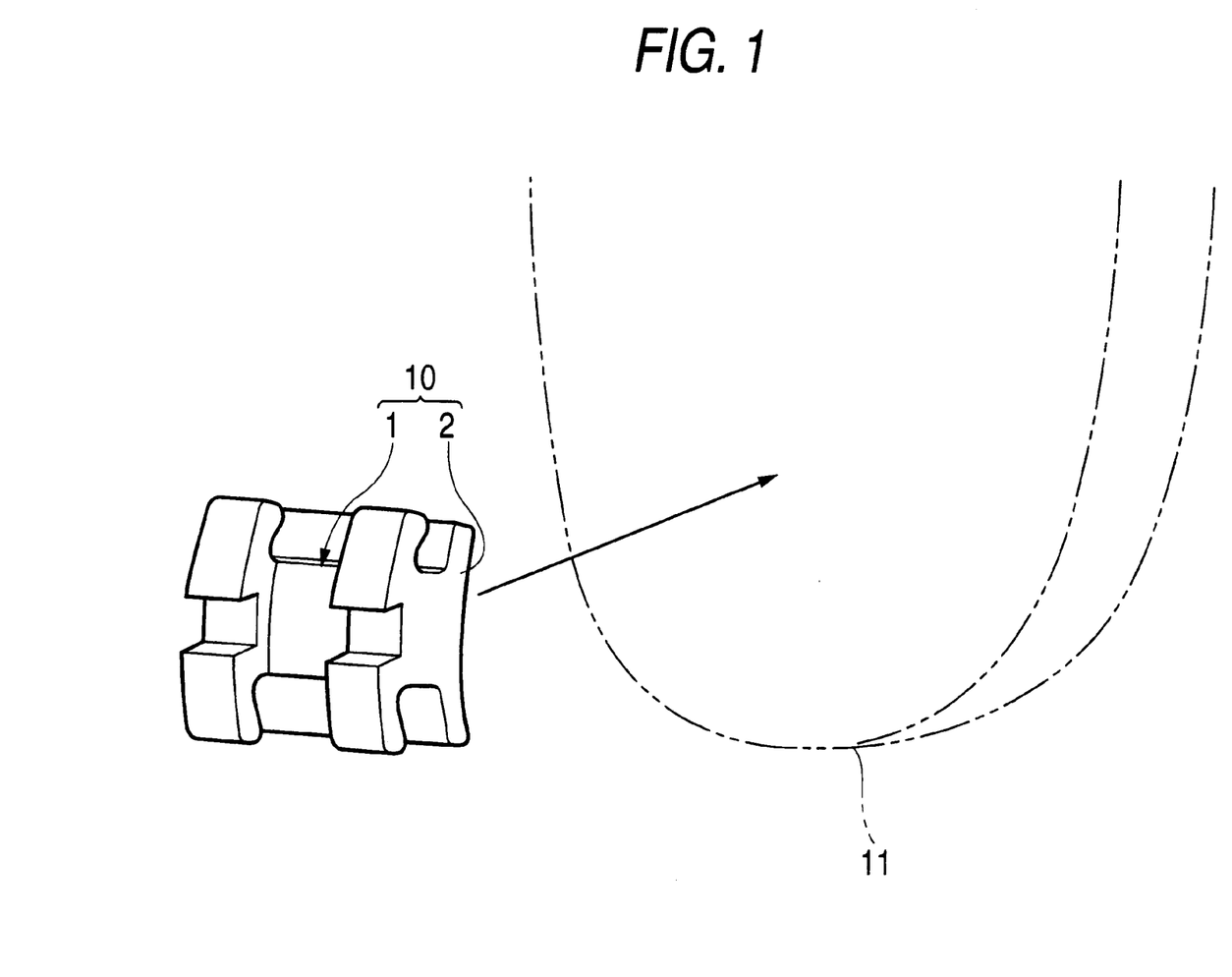
FIG. 1 is a perspective view of the bracket according to the embodiment of the invention.

As shown in FIG. 1, the orthodontic appliance according to a first embodiment of the invention is a bracket 10 comprising a main body 1 for orthodontic treatment of teeth 11 and a bonding base 2 connected to the main body 1 and capable of adhering to the teeth 11. The main body 1and the bonding base 2 each comprise the calcium phosphate crystallizing glass.

Technologies of applying the calcium phosphate crystallizing glass to tooth crown repairing materials, artificial dental roots and artificial bones are disclosed in JP-A-60-28911, 60-96544, 60-131835, 60-180931, 60-221342, 61-56111, 61-58836, 61-72638, 61-179143, 61-186247, 61-197463, 62-56334, 62-56335, 62-56337, 62-128947, 2-26846, 2-44039, 2-126884 and 4-18007.

The main body 1 of the bracket 10 and the bonding base 2 according to the invention can suitably be produced by melting glass raw material compositions described in the above publications and conducting conventional investment casting (see JP-A-60-131835, 1-301608, 2-25541U, and 3-39016U). There is no prior art using the calcium phosphate crystallizing glass as the orthodontic appliance.

The calcium phosphate crystallizing glass preferably comprises CaO 10 to 60 wt %, $P_2O_5$ 25 to 85 wt %, $Al_2O_3$ 5 to 25 wt %, and $Li_2O$ 0.01 to 5 wt %.

If CaO exceeds 60 wt % or $P_2O_5$ is less than 25 wt %, the melting temperature is high and vitrification is difficult. Reversely, if CaO is less than 10 wt % or $P_2O_5$ exceeds 85 wt %, the melting temperature lowers and the vitrification is easy, but a crystallizing treatment is difficult, and excessive phosphoric acid is set free, becoming chemically unstable.

On the other hand, if $Al_2O_3$ exceeds 25 wt %, the melting temperature is high and the vitrification is difficult. If it is less than 5 wt %, crystals of $Al_2O_3.P_2O_5$ do not generate or the amount of crystals generated is small, and it is difficult to avoid occurrence of internal defects such as air bubbles.

Further, if $Li_2O$ exceeds 5 wt %, it is chemically unstable, and if it is less than 0.01 wt %, it is difficult to obtain fine crystallized structure.

The aesthetic appreciation of the bracket 10 produced as above is excellent since the calcium phosphate crystallizing glass shows white semi-transparency. Where coloring agents (Fe, Ce, W, Ti, Ni, Ru and others) are added as needed, tints like a natural tooth can be developed.

The bonding base 2 of the bracket 10 is adhered to the teeth 11 via, e.g., an adhesive for the orthodontic purpose at the initiation of the orthodontic treatment. When the ceramic bracket is desired to securely adhere to the teeth, it is necessary to apply a silane coupling agent to the bonding base 2 or provide a mechanical lock.

The adhesion between the plastic bracket and the teeth via the adhesive relies on compatibility between the plastic and a solvent of the adhesive, and the adhesive strength has been insufficient.

However, the calcium phosphate crystallizing glass bracket 10 contains phosphorus and calcium which are enamel components of teeth, and in particular, an ion component of the calcium makes chelate combinations with various organic compounds contained in the adhesive. As a result, the adhesive strength suitable as the orthodontic appliance can be obtained without performing any special treatment to the bonding base 2.

Namely, it is regarded as ideal that the adhesive strength of the orthodontic appliance is 70 to 120N for anteriors (central incisor teeth, lateral incisor teeth and carine), 100 to 150N for premolar teeth and 150 to 200N for molar teeth, and the adhesive strength of around 10N per 1 $mm^2$ is demanded as a rough standard. According to the bracket 10 of the invention, the adhesive strength can be easily controlled within the ideal range.

If necessary, for example, a phosphorus acid etching may be carried out on the bonding base 2 to make the surface roughness being 10 μm or more based on JIS B0601. Preferably, the surface roughness is 10 to 100 μm. For the phosphorus acid etching, conventional phosphorus acid etching solution or phosphorus acid etching jelly belonging to the orthodontic adhesive can be used with out any limitation, and by the phosphorus acid etching treatment, the bracket 10 can be securely adhered to the teeth 11. Particularly, when using a small sized bracket or the orthodontic braces having a narrow space of the bonding base such as the buccal tube for a second molar tooth, the phosphorus acid etching is desirably carried out for steadily obtaining the adhesive strength.

Figure 2A:
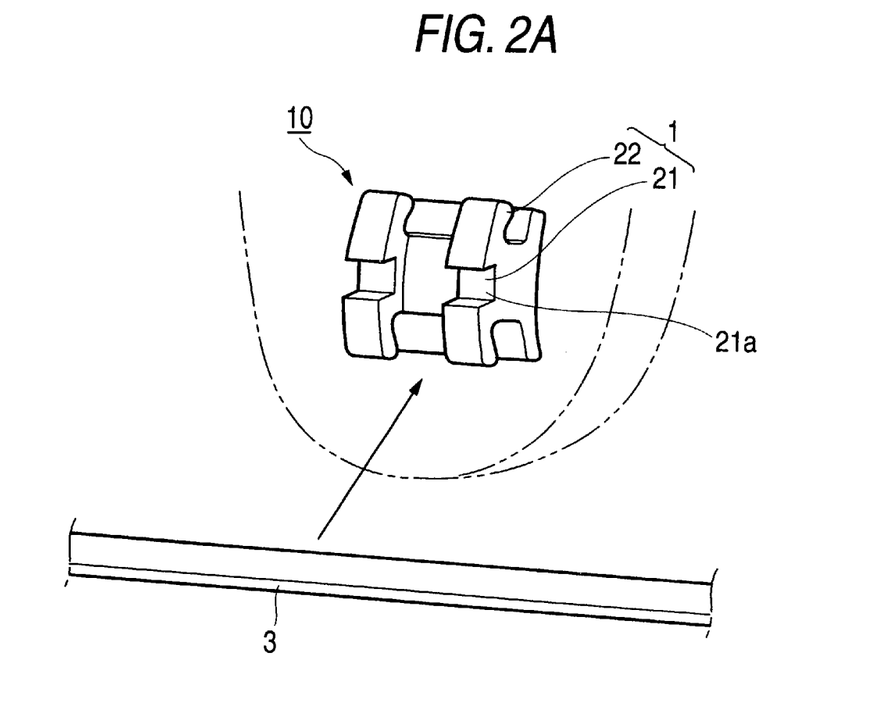
FIG. 2 is whole perspective views showing the embodiments of the invention.

The bracket 10 thus adhered to the teeth 11 has the main body 1 comprising slots 21 and tiewings 22 in the direction separating from the slots 21 serving as orthodontic means (see FIG. 2A). The bracket 10 and the archwire 3 are connected by inlaying the archwire 3 of square cross section into the slots 21, and ligating the tiewings 22 and the archwire 3 with a ligature wire 4 (see FIG. 2B). For other teeth (not shown), a bracket not shown) of the same structure as the bracket 10 is adhered, and the bracket adhered to the teeth is bridged by the archwire 3, so that the orthodontic treatment is started. As the archwire 3, an archwire circular in cross section may be used at an early stage of the treatment.

The slot 21 comprises the calcium phosphate crystallizing glass. As a result, the sliding of the archwire is good to the slot 21, and the slot is not necessarily made of metal as seen in the ceramic bracket.

Preferably, the slot 21 is composed by changing the composition of the calcium phosphate crystallizing glass such that dynamic frictional force is 0.98N (100 gr) or lower when pressing the bottom 21a of the slot 21 by the archwire 3 at load of 1.96N (200 gr), so that the sliding property can be surely made good. The material of the archwire 3 used is a metal such as alloys of stainless steel, cobalt-chromium, nickel-titanium, β-titanium and so on. Strictly, values of the dynamic frictional force vary depending on kinds of metals to be used when measuring the dynamic frictional force, but variances can be ignored within the above-described range (see the literature "The dynamic frictional resistance between orthodontic brackets and archwires" Tselepis et al. AJODO 1994; 106: 131 to 138).

Preferably, the main body 1 of the bracket 10 and the bonding base 2 are unified into one body with the calcium phosphate crystallizing glass of the same components, and the adhesive strength between the teeth 11 and bonding base 2 is 7 MPa or higher per unit area. As described above, by making the adhesive strength 7 MPa or higher, even if a patient takes an ordinary meal, the adhesion can be securely maintained over a period of 18 to 24 months which is considered as a general period of orthodontic treatment. The adhesion is assumed to use the adhesive for general purpose (organic adhesive), and the adhesive strength mainly depends on the composition of the calcium phosphate crystallizing glass and the surface conditions of the bonding base. That is, for example, the composition of the calcium phosphate crystallizing glass is adjusted or the surface conditions of the bonding base are designed such that the adhesive strength is 7 MPa or higher. The surface condition of the bonding base may be designed by sandblasting or phosphorus acid etching treatments.

It is desirable to use the calcium phosphate crystallizing glass having the bending strength of 100 MPa or higher based on JIS R1601 by changing the compositions of the calcium phosphate crystallizing glass, thereby securely decreasing the possibility of injuring the bracket 10 during the orthodontic treatment.

Incidentally, it is known that the calcium phosphate crystallizing glass, natural tooth enamel, aluminum oxide (called as alumina) ceramics, and zirconium oxide (called as zirconia) ceramics have respective hardness of values as shown in Table 1.

TABLE 1

| Material | Vickers hardness (GPa) |
| --- | --- |
| Calcium phosphate Crystallizing glass *1 | 4.1 |
| Enamel of natural tooth *1 | 3.8 |
| Alumina ceramics *2 | 15.6 to 17.0 |
| Zirconia ceramics *2 | 13.7 to 14.7 |

*1 MATSURI, Hirohito: Dental technic and clinic of calcium phosphate based castable-ceramics "Crycera", Quintessence of Dental Technology, Vol. 21, No. 6, P. 95–105 1996
*2 From Ceramics data book 2000 "Industry and Products: vol. 28, No. 82", P. 222 TYK Fine Ceramics Product Materials, issued by Kougyo Seihin Gijutsu Kyokai (Kabushiki Kaisha Techno Plaza) 2000

As shown in Table 1, the hardness (Vickers hardness) of the calcium phosphate crystallizing glass containing CaO 19 wt %, $P_2O_5$ 69 wt %, $Al_2O_3$ 5 wt % and $Li_2O$ 1.5 wt % shows the lower value than those of alumina ceramics and zirconia ceramics, and is substantially equivalent to the hardness of the tooth enamel.

Accordingly, the calcium phosphate crystallizing glass bracket 10 does not have the possibility of wearing the opposite teeth during the orthodontic treatment. (For securely decreasing the possibility of wearing the opposite teeth, it is desirable to vary the composition of the calcium phosphate crystallizing glass so as to make Vickers hardness Hv of the bracket 4.5 GPa or lower.)

In addition, when debonding the bracket 10 from the teeth 11 after the treatment, excessive force is not required, so that there is little possibility of injuring enamel of the teeth.

It is known that plaque is difficult to adhere on the surface of the calcium phosphate crystallizing glass (see In-vitro test described in vol. 10, No. 1, 102 to 116 (1991) Dental Materials and Equipment, "Experimental study concerning Surface conditions of calcium phosphate crystallizing glass and adherence of streptococcus mutans"), and the calcium phosphate crystallizing glass bracket 10 is very hygienic during the orthodontic treatment.

The bracket 10 has been explained as the orthodontic appliance according to the first embodiment of the invention, but the slot of the main body may be provided in the inside thereof with a metal slot liner of U shape in transversally cross section in order to appropriately increase strength of the bracket according to kinds or shapes of the teeth to which the bracket is adhered.

Figure 3:
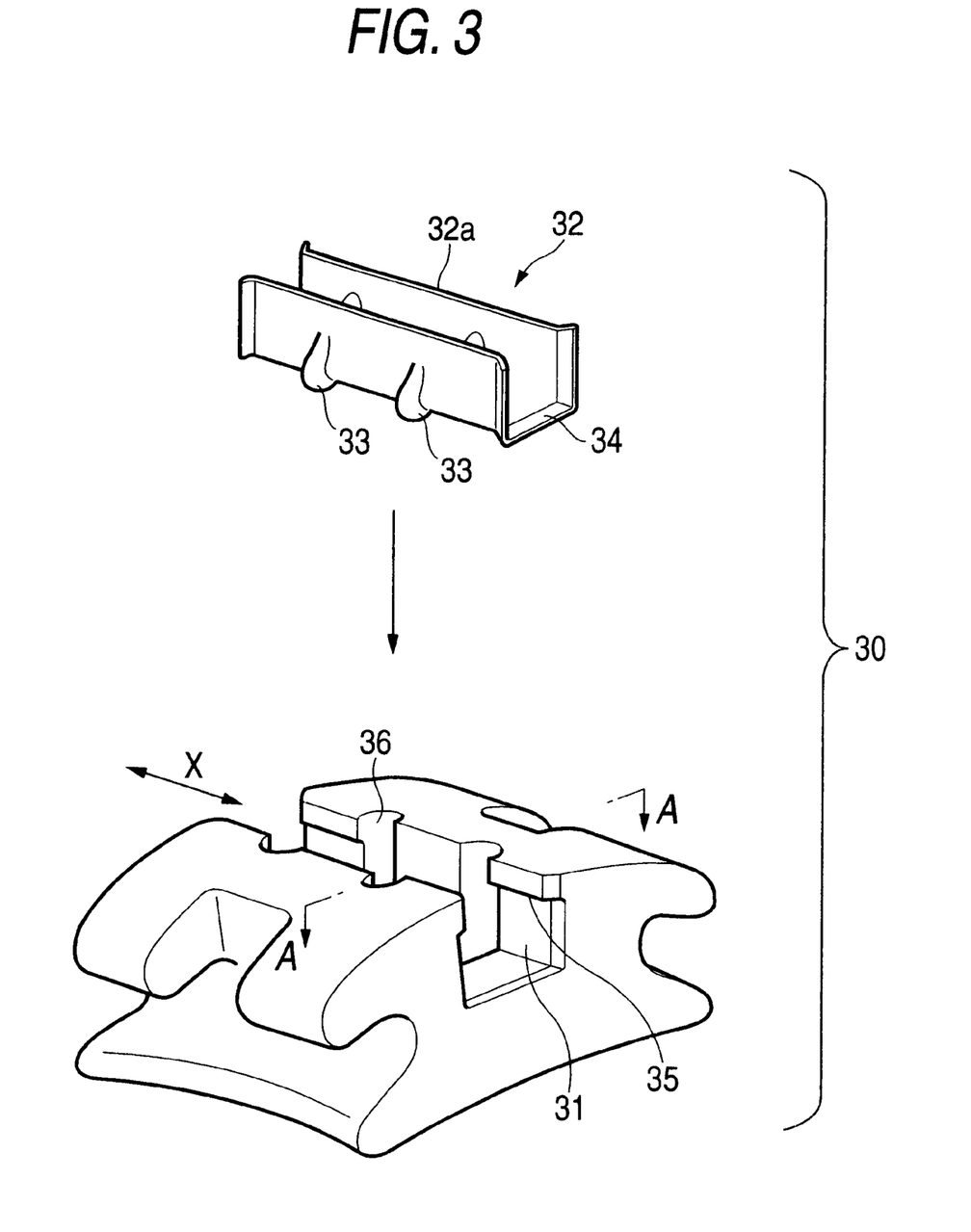
FIG. 3 is perspective views of the other bracket according to the embodiment of the invention.

FIG. 3 shows a structure for more increasing strength of the bracket. In a case of the orthodontic appliance according to a second embodiment of the invention, the bracket 30 has a constitution that a metal slot liner 21 of U shape in transversally cross section is embedded in the slot 31.

Figure 4:
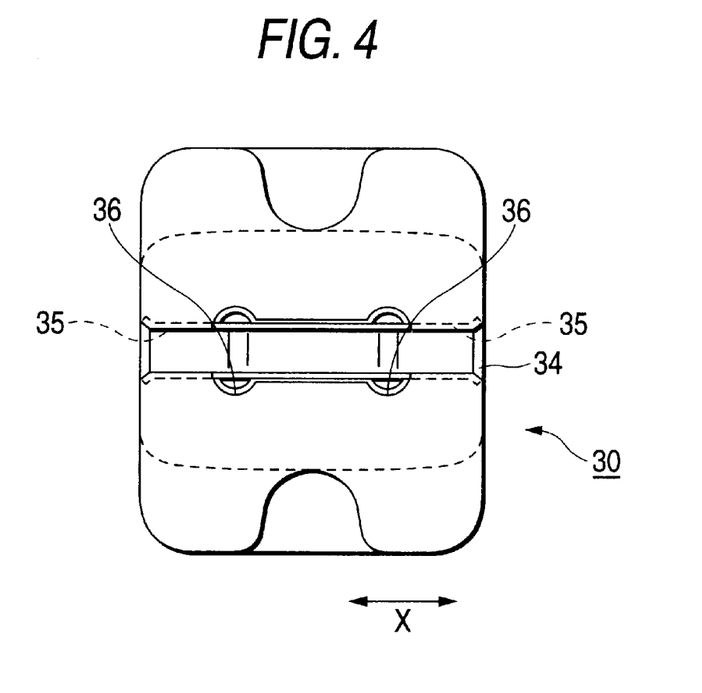
FIG. 4 is a plane view of other the bracket according to the embodiment of the invention, seen from the slot side.

The metal slot liner 32 has beads 33 expanding in width direction, thereby preventing the metal slot liner 32 from sliding in a lengthwise direction X to the slot 31. In more detail, as shown in FIG. 4, under a state that the metal slot liner 32 is mounted, the beads 33 are fitted in recess portions 36 of the slot 31 to restrain the slot liner 31 from moving in the lengthwise direction. In addition, the metal slot liner 32 are provided with flares 34 curved at appropriate radius of curvature at ends in the mesiodistal direction, thereby preventing the archwire from biting at the ends in the mesiodistal direction of the metal slot liner 32 and also preventing the sliding property from decreasing.

Examples of the material of the metal slot liner 32 include β-titanium alloy of Ti-15Mo-5Zr-3Al and Ti—Nb—Sn alloy. Those alloys make it possible to produce the metal slot liner 32 having excellent processability and high strength, and which is difficult to cause allergy substances.

Figure 5:
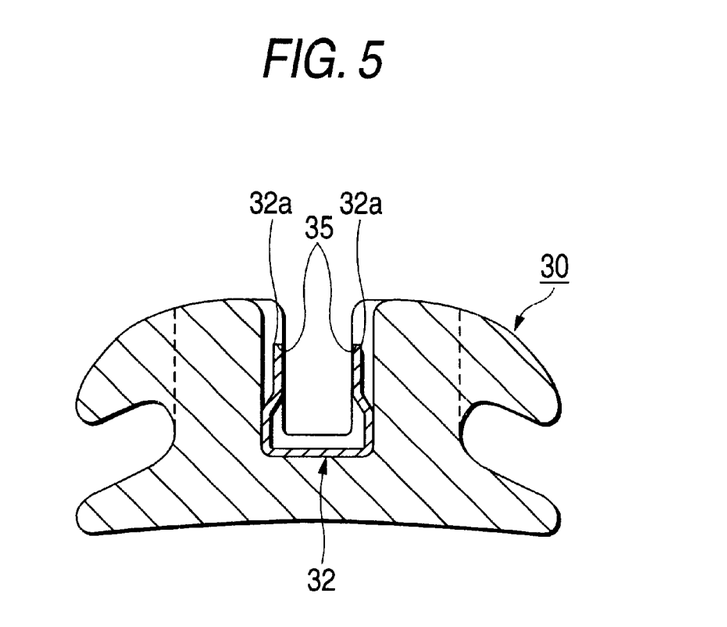
FIG. 5 is a partially cross sectional view taken along A—A line in FIG. 3.

The bracket 30 has steps 35 at the slot 31, and as shown in FIG. 5, upper portions 32a of the metal slot liner 32 and the step 35 are entangled with each other, so that the metal slot liner 32 is engaged with the slot 31.

Other than the above-described bracket 30, a bracket may be made where a metal slot liner is adhered to the inside of the slot 31 by a dental adhesive.

The embodiments of the invention has been explained above, but shapes, dimensions, forms, number, disposing positions and others of the main body, the slots of the main body and the tiewings are not particularly limited so long as those can attain the invention.

In the embodiments, the invention has been explained using the bracket, but the invention can be applied to other orthodontic appliances such as the orthodontic braces of directly adhering to tooth crowns such as buccal tubes, sheaths, buttons, lingual attachments, and the like other than the brackets.

The invention will be described in more detail by reference to the following Examples and Comparative Examples, but it should be understood that the invention is not construed as being limited.

Production of Brackets of the Example (Calcium Phosphate Crystallizing Glass Bracket):

Glass raw material composition comprising CaO 19 wt %, $P_2O_5$ 69 wt %, $Al_2O_3$ 10 wt % and $Li_2O$ 1.5 wt % was cast according to the conventional investment casting method to prepare brackets of the Example in the following manners.

Using a mold which can produce the structures of the same shapes as the bracket 10 shown in FIG. 1, more specifically, the structures of the same shape as an upper carine left bracket (Orthoesta® (0.018" slot size, and bonding area being 12 mm²), trade name of Tommy Inc.), a plastic bracket model in which a main body and a bonding base were integrally unified, was produced (the plastic was a thermoplastic polypropylene).

The plastic bracket thus produced was implanted in a wax sprue, and thus produced wax sprue connected to a wax tree was then embedded in a slurry of a phosphate-type investment material which had been subjected to vacuum defoaming (trade name: "Crycera investment material", made by Kyutai Dentoceram Inc.). The slurry of the phosphate-type investment material was cured to obtain a phosphate embedding material to have the plastic bracket embedded therein.

The curedphosphate-type investment material after curing was heated and baked at 800° C. for 40 min to melt out the plastic bracket and the wax tree from the investment material, thereby producing a cast model having a cavity (vacancy) of a shape that the bracket was connected to the tree.

A molten glass obtained by heating the glass raw material composition at 1310° C. was introduced under pressure into the cavity of the cast moldmade of the phosphate investment material. After casting, the glass cast body was taken out of the casting mold of the phosphate investment material by the sand blasting method. The cast glass was heated at 560 to 570° C. for 12 hours, and then heated at 640° C. for 2 hours, to thereby conduct a crystallizing treatment (precipitation of crystals of β-calcium metaphosphate). Finally, the crystallized glass product was subjected to a barrel grinding to conduct surface finishing, thereby obtaining the bracket of the Example (calcium phosphate crystallizing glass bracket).

In comparison with the initially produced plastic bracket, the bracket of the Example had shrinkage percentage as small as 0.6%, and dimensional change as compared with the plastic bracket model could substantially be ignored. Thus, the dimension of the slot in which the archwire was inlaid can secure precision within around 20 μm, and any special post-treatment is not required. As a result, the bracket of high dimensional precision could be obtained.

Adhesive Strength Test of Bracket of the Example:

Two kinds of adhesives for the orthodontic treatment, "Super Bond" (made by Sun Medical Inc.) and "Ortho-Lock Bond" (made by GAC International Inc.), were applied to the bonding bases of the brackets of the Example (Sample Nos. 1 to 5), and were adhered to the ends of an acrylic resin adherend (diameter: 8 mm and thickness: 10 mm), followed by allowing to stand at 37° C. for 24 hours. Adhesive strength tests in shearing and tension of the bracket were conducted in dry atmosphere using an electronic universal tensilometer, Model No. 5567 (made by Instron Inc.). The test results obtained are shown in Table 2 below.

TABLE 2

| Sample No. | Adhesive strength (N) Adhesion by Super Bond | (Values in terms of kgf) Adhesion of Ortho-Lock |
|---|---|---|
| 1 | 162 (16.5) | 133 (13.6) |
| 2 | 100 (10.2) | 185 (18.9) |
| 3 | 113 (11.5) | 155 (15.8) |
| 4 | 125 (12.8) | 122 (12.5) |
| 5 | — (—) | 172 (17.5) |
| Average | 125 (12.7) | 154 (15.7) |

Adhesive strength of the brackets of the Examples

As described above, the adhesive strength of the bracket is desirably about 10N per 1 mm². Therefore, since the area in the bonding base of the brackets in the Example is 12 mm², the adhesive strength is preferably about 120N.

As shown in Table 2 above, according to the brackets of the Example, although any additional pre-treatment for increasing adhesive strength to the bonding base was not conducted, it was confirmed that the desired adhesive strength can be obtained.

Figure 2B:
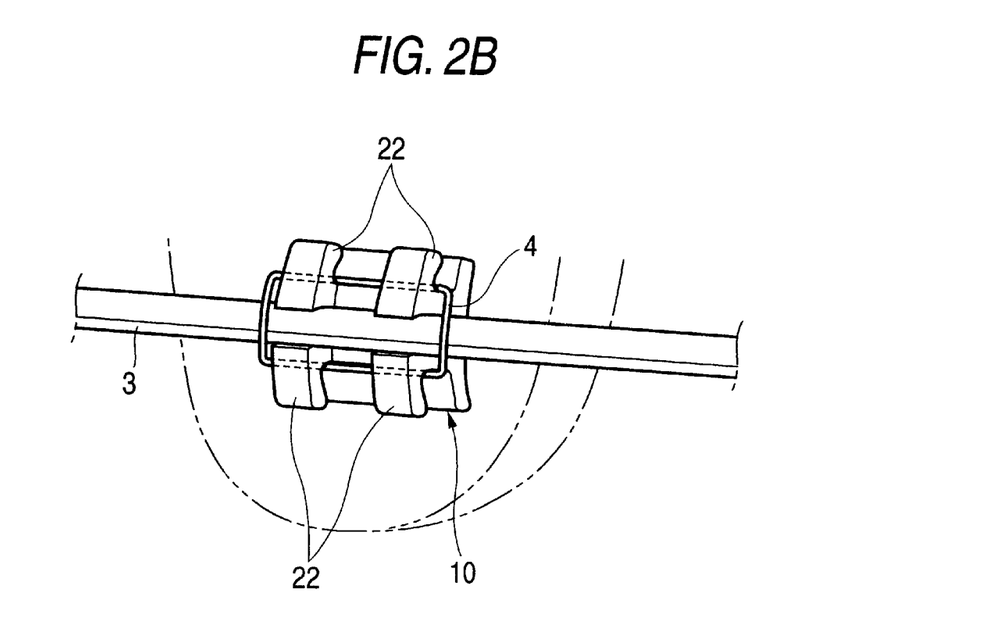

Sliding Property Test to Rectangular Archwire of the Bracket:

"0.017"×0.025" rectangular archwire (stainless steel)" (made by GAC International Inc.) was inlaid in the slots of the main bodies of the brackets (Sample Nos. 1 to 5) in the Example, and the rectangular archwire and the tiewings were ligated as shown in FIG. 2B using a polyurethane elastmeric ligature ring "ERL 990" (made by GAC International Inc., trade name: Las-Tie). The bonding base of the bracket was fixedly adhered, and at the same time, the rectangular archwire was pressed to the bottom of the slot at the load of 1.96N (200 gr), and dynamic frictional force when moving the rectangular archwire in the longitudinal direction at a rate of 1.3 mm/min was measured with a load tester "Model 1305D" Aiko Engineering Inc. (maximum and minimum frictional force when moving the rectangular archwire were measured) so as to conduct the sliding property tests to the rectangular archwire of the bracket.

Similar tests of the sliding property were performed on ceramic bracket "Crystaline®" (made by Tommy Inc.), plastic bracket with the metal insert "Orthoesta® (made by Tommy Inc.), and metal bracket "Omni Arch®" (made by Tommy Inc.) of the same shapes as the brackets of the Example.

It can be said that the lower the value of the dynamic frictional force of the bracket, the more excellent the sliding property to the rectangular archwire.

The test results of the sliding property are shown in Table 3 below. The lower limit of the dynamic frictional force corresponds to the above-described minimum frictional force, and the upper limit of the dynamic frictional force corresponds to the maximum frictional force. Further, regarding the Example, the lower limits are the average values when measuring the minimum frictional force of the samples Nos. 1 to 5, and the upper limits are the average values when measuring the maximum frictional force of the samples Nos. 1 to 5.

TABLE 3

| | Brackets | Dynamic frictional force (N) |
|---|---|---|
| Example | A | 0.64 to 0.74 (65 to 75) |
| Comparative | B | 1.03 to 1.57 (105 to 160) |
| Example | C | 0.69 to 1.03 (70 to 105) |
| | D | 1.37 to 1.72 (140 to 175) |

Notes:
Values in ( ) are in terms of gr.
A: Calcium phosphate crystallizing glass bracket
B: Ceramic bracket
C: Plastic bracket with metal insert
D: Metal bracket As shown in Table 3, it was confirmed that the dynamic fictional force when using the bracket of the Example (calcium phosphate crystallizing glass bracket) showed the lowest value and the sliding property was most preferable.

The bracket slides on and off along the archwire or stops in the actual orthodontic treatment. Therefore, it is regarded that the friction between the bracket and the archwire is effected by alternate repetition of the dynamic friction and the static friction.

A method of continuously sliding the archwire ligated to the slot of the bracket and measuring the frictional force during this sliding period by the universal tester is generally known as a method of evaluating friction of the bracket and the archwire. This method obtains a graph having a plurality of peaks in the direction of the axis of ordinate when the moving amount of the archwire is shown on an axis of abscissa, and the frictional force between the bracket and the archwire is shown on an axis of ordinate. Therefore, for example, the frictional force is averaged as to peaks other than a first peak at initiation of sliding, thereby evaluating the friction between the bracket and the archwire in terms of the dynamic frictional force.

Almost all of research papers relating to the evaluation of the friction between the bracket and the archwire show methods of evaluating the dynamic frictional force. From this fact, in the invention, the maximum frictional force and the minimum frictional force are measured using a plurality of samples, and the sliding property is evaluated using the average values of the minimum frictional force and the average values of the maximum frictional force.

Observation Test on Rupture Surface of the Bracket:

The tests were carried out using the brackets of the Example, monocrystal alumina ceramic bracket ($Al_2O_3$: 100 wt %) and polycrystal alumina ceramic bracket ($Al_2O_3$: 99.6 wt % and MgO: 0.4 wt %). The monocrystal alumina ceramic bracket is produced by a method disclosed in JP-A-60-234656. The polycrystal alumina ceramic bracket is produced by forming alumina powder into compact and sintering the same at high temperatures. Fragments scattered when forcibly breaking the tiewings of these brackets were shown in stereoscopic photographs of 20 magnifications. The photograph of the rupture surface of the bracket of the Example is shown in FIG. 6, the photograph of the rupture surface of the monocrystal alumina ceramic bracket is shown in FIG. 7, and the photograph of the rupture surface of the polycrystal alumina ceramic bracket is shown in FIG. 8.

Figure 6:
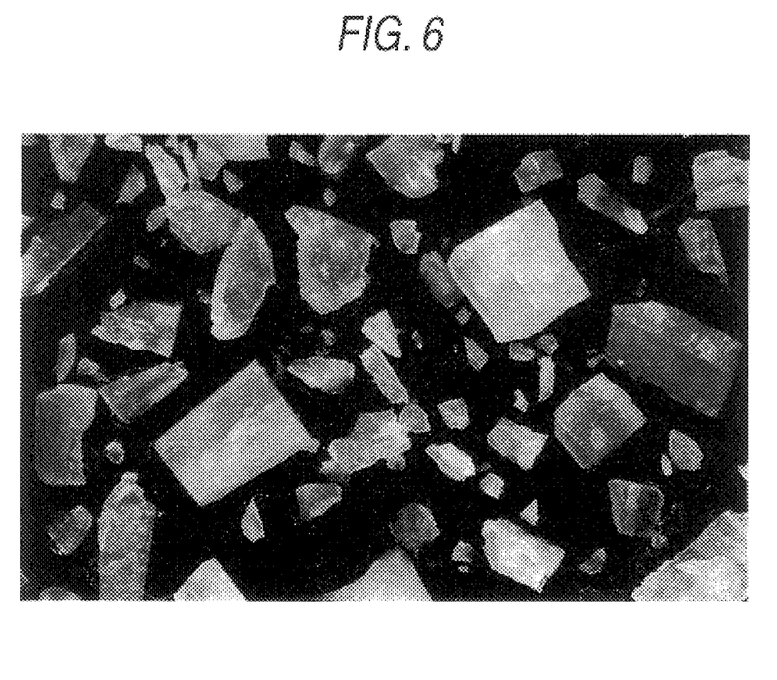
FIG. 6 is a photograph of cut area of the bracket of the Example.
Figure 7:
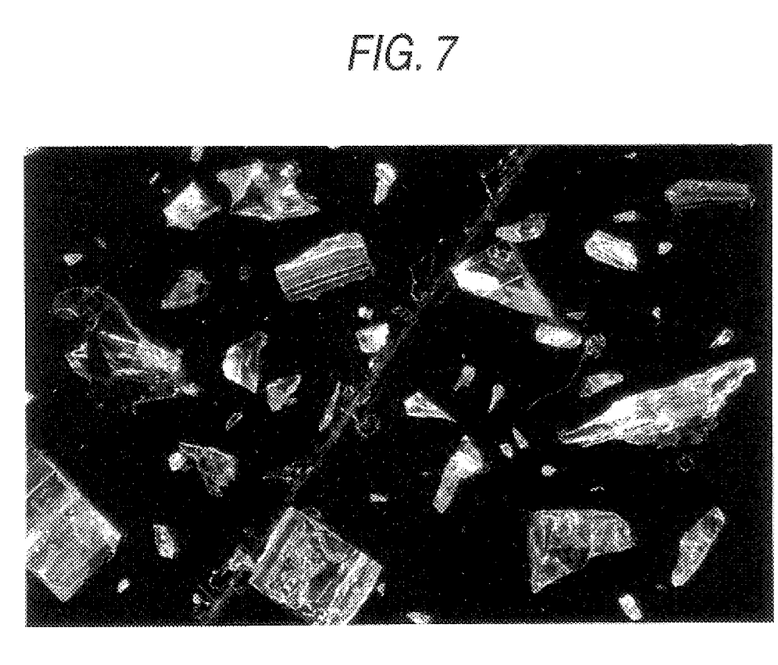
FIG. 7 is a photograph of cut area of the monocrystal alumina ceramic bracket.
Figure 8:
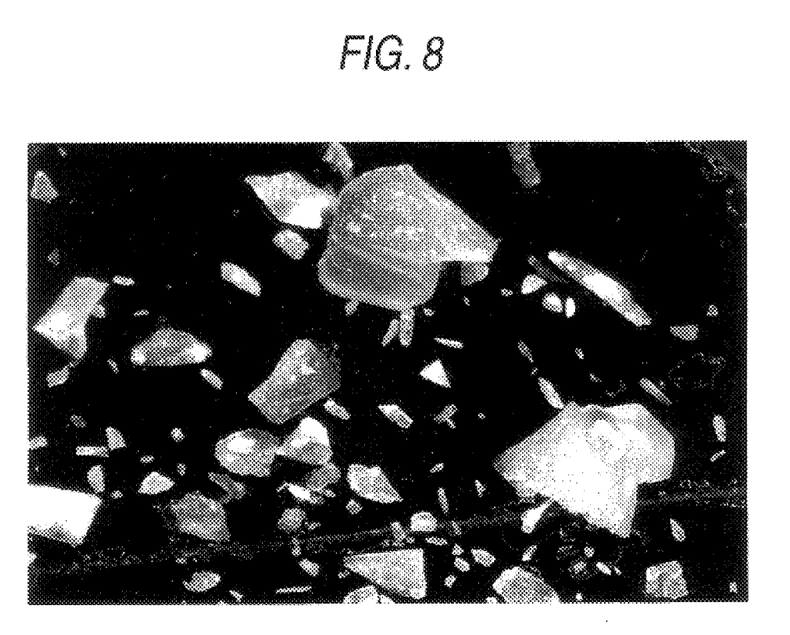
FIG. 8 is a photograph of cut area of the polycrystal alumina ceramic bracket.

As shown in FIGS. 6 to 8, it was confirmed that the rupture surfaces of the monocrystal alumina ceramic bracket and the polycrystal alumina ceramic bracket are sharp, while the rupture surface of the bracket of the Example is comparatively granule. Thus, according to the bracket of the Example, even if being broken, the rupture surface is granule, so that the oral cavity is not injured.

According to the invention, the main body and the bonding base each comprise a calcium phosphate crystallizing glass. Therefore, it is possible to provide an orthodontic appliance having all of the following elements 1) to 9):

1) production cost can be decreased;
2) aesthetic appreciation is excellent;
3) sufficient strength and durability as the orthodontic appliance are provided;
4) an allergy causing substance is difficult to occur;
5) adhesion to the teeth is secured;
6) the opposite teeth are less to be worn during the orthodontic treatment;
7) plague causing decayed teeth or periodical diseases are difficult to adhere to the bracket during the orthodontic treatment;
8) debonding from the teeth is easy after the orthodontic treatment; and
9) in case that the orthodontic appliance allows engagement with the archwire for straightening the teeth, the sliding property is excellent to the archwire.

What is claimed is:

1. An orthodontic appliance comprising a main body for orthodontic treatment and a bonding base connected to the main body and capable of adhering to the teeth, wherein the main body and the bonding base each comprise calcium phosphate crystallizing glass.

2. The orthodontic appliance as claimed in claim 1, wherein the calcium phosphate crystallizing glass comprises CaO 10 to 60 wt %, $P_2O_5$ 25 to 85 wt %, $Al_2O_3$ 5 to 25 wt % and $Li_2O$ 0.01 to 5 wt %.

3. The orthodontic appliance as claimed in claim 1, wherein the calcium phosphate crystallizing glass has Vickers hardness Hv based on JIS Z2244 of 4.5 GPa or lower, and bending strength based on JIS R1601 of 100 MPa or higher.

4. The orthodontic appliance as claimed in claim 1, wherein the main body and the bonding base are integrally formed with the calcium phosphate crystallizing glass having the same components, and adhesive strength between the teeth and the bonding base is 7 MPa or higher per unit area.

5. The orthodontic appliance as claimed in claim 4, wherein the bonding base has a surface roughness based on JIS B0601 of 10 $\mu$m or more.

6. The orthodontic appliance as claimed in claim 1, wherein the main body has slots as orthodontic means.

7. The orthodontic appliance as claimed in claim 6, wherein dynamic frictional force when an archwire is pressed against the bottom of the slot at 1.96 N (200 gr) is 0.98 N (100 gr) or lower.

8. The orthodontic appliance as claimed in claim 6, wherein the slots are provided with a metal slot liner of U shaped cross section in the inside thereof.

* * * * *